United States Patent [19]

Ohlendorf et al.

[11] Patent Number: 4,672,062
[45] Date of Patent: Jun. 9, 1987

[54] 3-AMINO-2,3-DIHYDRO-1-BENZOXEPINE COMPOUNDS AND PHARMACEUTICAL COMPOSITIONS CONTAINING THEM

[75] Inventors: Heinrich-Wilhelm Ohlendorf, Garsbsen; Michael Ruhland, Hanover; Klaus-Ullrich Wolf, Haenigsen, all of Fed. Rep. of Germany

[73] Assignee: Kali-Chemie Pharma GmbH, Hannover, Fed. Rep. of Germany

[21] Appl. No.: 794,761

[22] Filed: Nov. 4, 1985

[30] Foreign Application Priority Data

Nov. 5, 1984 [DE] Fed. Rep. of Germany ....... 3440296

[51] Int. Cl.⁴ ................. C07D 417/04; C07D 413/04; C07D 405/04; C07D 313/08; A61K 31/335; A61K 31/40; A61K 31/535; A61K 31/495
[52] U.S. Cl. .................................... 514/227; 514/239; 514/254; 514/320; 514/422; 514/222; 514/256; 514/450; 544/147; 544/63; 544/96; 544/62; 544/55; 544/3; 544/376; 544/238; 544/333; 546/269; 548/525; 549/355
[58] Field of Search ................ 549/355; 514/450, 222, 514/256, 422, 227, 239, 254, 320; 548/525; 546/269; 544/147, 376, 238, 333, 62, 63, 55, 3, 96

[56] References Cited

U.S. PATENT DOCUMENTS 4,279,904 7/1981 Ohlendorf et al. ................. 549/350

Primary Examiner—Norma S. Milestone
Attorney, Agent, or Firm—Schwartz, Jeffery, Schwaab, Mack, Blumenthal & Evans

[57] ABSTRACT 3-amino-2,3-dihydro-1-benzoxepine compounds corresponding to the general Formula I

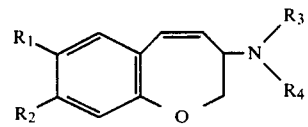

wherein $R_1$ and $R_2$ may each be hydrogen, halogen, lower alkyl or lower alkoxy, or if one of $R_1$ and $R_2$ is hydrogen, the other may also be nitro or trifluoromethyl, $R_3$ represents hydrogen or a lower alkyl group which optionally may be substituted by hydroxy, lower alnoxy, an optionally substituted phenyl group or an optionally substituted amino group, and $R_4$ represents hydrogen or lower alkyl, or $R_3$ and $R_4$ together with the nitrogen atom form a 5 or 6 member heterocycle. The compounds exhibit pharmacological, especially antidepressive, activity.

5 Claims, No Drawings

3-AMINO-2,3-DIHYDRO-1-BENZOXEPINE COMPOUNDS AND PHARMACEUTICAL COMPOSITIONS CONTAINING THEM

BACKGROUND OF THE INVENTION

The present invention relates to new 3-amino-2,3-dihydro-1-benzoxepine compounds and their acid addition salts as well as pharmaceutical preparations containing these compounds and processes for producing such compounds.

2,3,4,5-tetrahydro-3-amino-1-benzoxepine-5-ol compounds are known from U.S. Pat. No. 4,279,904, having activities which favorably influence stomach motility.

SUMMARY OF THE INVENTION

It is the object of the present invention to provide new 3-amino-2,3-dihydro-1-benzoxepine derivatives with valuable pharmacological properties.

These and other objects of the invention are achieved by providing 3-amino-2,3-dihydro-1-benzoxepine compounds corresponding to Formula I:

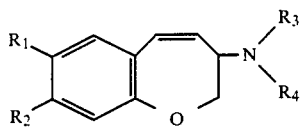

wherein
$R_1$ represents hydrogen, halogen, lower alkyl or lower alkoxy, and
$R_2$ represents hydrogen, halogen, lower alkyl or lower alkoxy, or
one of the substituents $R_1$ and $R_2$ is hydrogen and the other represents a nitro group or trifluoromethyl group,
$R_3$ represents hydrogen, a lower alkyl group or a lower alkyl group which is substituted on a carbon atom not bound to nitrogen by hydroxy, lower alkoxy, or a phenyl group corresponding to Formula a

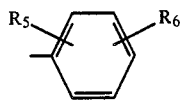

wherein $R_5$ represents hydrogen, halogen, lower alkyl or lower alkoxy, and
$R_6$ represents hydrogen, halogen, lower alkyl or lower alkoxy, or
$R_5$ and $R_6$ are bonded to adjacent carbon atoms and together represent an alkylene dioxy group having one or two carbon atoms,
or by an amino group corresponding to Formula b

wherein $R_7$ represents hydrogen or lower alkyl, and
$R_8$ represents hydrogen or lower alkyl, or $R_7$ and $R_8$ together with the nitrogen atom to which they are bonded form a 5 or 6 member heterocycle which may include as a second heteroatom oxygen, sulfur or an $=NR_9$ group in which $R_9$ represents hydrogen or lower alkyl, and
$R_4$ represents hydrogen or lower alkyl, or
$R_3$ and $R_4$ together with the nitrogen atom to which they are bonded form a 5 or 6 member heterocycle which may contain as a second heteroatom oxygen, sulfur or an $=NR_{10}$ group in which $R_{10}$ represents hydrogen, lower alkyl, benzyl or benzyl substituted in the phenyl ring with 1 or 2 substituents selected from halogen, lower alkyl, or lower alkoxy,
and their acid addition salts.

DETAILED DESCRIPTION OF PREFERRED EMBODIMENTS

It has now been found that the new 3-amino-2,3-dihydro-1-benzoxepine compounds have valuable pharmacological characteristics and are particularly distinguished by properties typical of antidepressives. Due to their pharmacological properties, the compounds are useful as medicaments, particularly in preparations for treatment of illnesses involving depression.

The present invention therefore relates to new 3-amino-2,3-dihydro-1-benzoxepine compounds corresponding to the Formula I

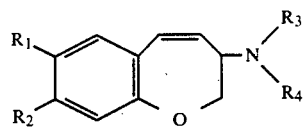

wherein
$R_1$ represents hydrogen, halogen, lower alkyl or lower alkoxy, and
$R_2$ represents hydrogen, halogen, lower alkyl or lower alkoxy, or
one of the substituents $R_1$ and $R_2$ is hydrogen and the other is nitro or trifluoromethyl,
$R_3$ represents hydrogen, a lower alkyl group or a lower alkyl group substituted on a carbon atom not bound to nitrogen by hydroxy, lower alkoxy or a phenyl group corresponding to the Formula a

wherein
$R_5$ represents hydrogen, halogen, lower alkyl or lower alkoxy, and
$R_6$ represents hydrogen, halogen, lower alkyl or lower alkoxy, or
$R_5$ and $R_6$ are bound to adjacent carbon atoms and together represent alkylenedioxy with 1-2 carbon atoms, or by an amino group corresponding to the Formula b

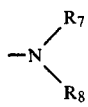

wherein
$R_7$ represents hydrogen or lower alkyl, and
$R_8$ represents hydrogen or lower alkyl, or R7 and R8 together with the nitrogen atom to which they are bound form a 5 or 6 member heterocycle which optionally may include a second hetero member selected from the group consisting of oxygen, sulfur or an =NR9 group in which R9 represents hydrogen or lower alkyl, and R4 represents hydrogen or lower alkyl, or R3 and R4 together with the nitrogen atom to which they are bound form a 5 or 6 member heterocycle which optionally may include a second hetero member selected from the group consisting of oxygen, sulfur or an =NR10 group wherein R10 represents hydrogen, lower alkyl, benzyl or benzyl substituted in the phenyl ring by 1 or 2 substituents selected from the group consisting of halogen, lower alkyl and lower alkoxy, and their acid addition salts.

Insofar as the Substituents $R_1$, $R_2$, $R_3$ and $R_4$ represent or contain lower alkyl groups, such groups may be straight chain or branched and preferably contain from 1 to 4 carbon atoms, most preferably 1 or 2 carbon atoms.

The substituents $R_1$ and $R_2$ preferably represent hydrogen or also halogen, lower alkyl or lower alkoxy. The halogen substituents $R_1$ and $R_2$ may be fluorine, chlorine or bromine, preferably chlorine. Insofar as $R_1$ and/or $R_2$ represent lower alkyl, they are preferably methyl or ethyl. Lower alkoxy substituents are most preferably methoxy.

The substituents $R_3$ and $R_4$ preferably represent hydrogen or lower alkyl or form together with the nitrogen atom to which they are bound a 5 or 6 member heterocyclic ring. It is particularly preferred that $R_3$ and $R_4$ represent hydrogen or lower alkyl. The lower alkyl groups may be straight chain or branched alkyl groups such as, for example, methyl, ethyl, n-propyl, isopropyl, n-butyl, or branched butyl. Compounds in which one of the substituents $R_3$ and $R_4$ is hydrogen, methyl or ethyl and the other is one of the aforementioned lower alkyl groups have proved to be advantageous.

If $R_3$ and $R_4$ together with the nitrogen atom to which they are bound form a heterocycle which contains a second heteroatom, the second hetero member may particularly desirably be oxygen or an imino group =NR10 in which R10 preferably represents benzyl or lower alkyl.

The lower alkoxy substituents of alkyl group $R_3$ may preferably be methoxy or ethoxy. If $R_3$ is substituted by a phenyl group corresponding to Formula a, the same preferences set forth above with respect to $R_1$ and $R_2$ also apply to the phenyl substituents $R_5$ and $R_6$. If $R_3$ is substituted by an amino group corresponding to Formula b, the amino substituents $R_7$ and $R_8$ may preferably be any of the aforementioned alkyl groups, particularly methyl or ethyl, or also hydrogen.

The new 3-amino-2,3-dihydro-1-benzoxepine compounds of Formula I are produced in accordance with the invention by splitting off, i.e. eliminating, a molecule of water from 3-amino-2,3,4,5-tetrahydro-1-benzoxepin-5-ol compounds corresponding to the Formula II

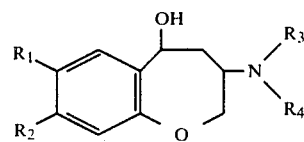

wherein $R_1$, $R_2$, $R_3$ and $R_4$ have the above meanings, and in appropriate circumstances converting the free compounds of Formula I to acid addition salts or converting the acid addition salts into the free compounds of Formula I.

The elimination of water from the 3-amino-2,3,4,5-tetrahydro-1-benzoxepin-5-ols of Formula II may be effected in accordance with conventional techniques for dehydration of alcohols by treatment with acid, water-eliminating agents.

For example, the compounds of Formula II may be treated with aqueous solutions of inorganic or organic acids whose are inert under the reaction conditions, optionally with the addition of an inert organic solvent which is miscible with water. Advantageously, strong inorganic acids are utilized for the water elimination. Examples of suitable inorganic acids include hydrogen halide acids such as hydrochloric acid or hydrobromic acid, e.g. an aqueous 5 to 32 percent hydrochloric acid solution, or phosphoric acid or sulfuric acid. Suitable organic acids are strong organic acids, for example benzene sulfonic acids, which may optionally be substituted in the benzene ring by lower alkyl or halogen, or lower aliphatic halocarboxylic acids, such as trifluoroacetic acid. Suitable water-miscible solvents, which may optionally be added to the reaction mixture, include lower alcohols in particular. The reaction temperature and the reaction time may vary depending on the strength of the acid utilized for the water elimination. Thus, depending on the concentration and the type of acid utilized, temperatures between room or ambient temperature and the boiling temperature of the reaction mixture may be utilized, and the reaction times may amount to from about one to several hours.

The compounds of Formula II may also be reacted with Lewis acids in a polar, aprotic, organic solvent in order to split off water. Aluminium chloride may desirably be utilized as the Lewis acid. Suitable solvents include lower alkyl ethers of lower polyols, e.g. lower glycol ethers such as ethylene glycol dimethyl ether. The reaction advantageously takes place at elevated temperature, particularly at temperatures between about 50 degrees C. and the boiling temperature of the reaction mixture.

The compounds of Formula I can be isolated from the reaction mixture and purified in known ways. Acid addition salts can be converted in the usual way into the free bases, and the free bases, can, if desired, be converted in a known manner into pharmaceutically acceptable acid addition salts. Suitable pharmaceutically acceptable acid addition salts of the compounds of Formula I include, for example, their salts with inorganic acids, e.g. hydrogen halide acids, particularly hydrochloric acid, sulfuric acid or phosphoric acid, or with organic acids, for example lower aliphatic monocarboxylic or dicarboxylic acids such as lactic acid, maleic acid, fumaric acid or acetic acid, or sulfonic acids, for example lower alkyl sulfonic acids such as methane sulfonic acid, benzene sulfonic acid or benzene sulfonic acids which are substituted in the benzene ring by halogen or lower alkyl such as p-toluene sulfonic acid, or cyclohexylamino sulfonic acid.

The compounds of Formula I contain an asymmetric carbon atom and exist in D- and L-forms. The present invention includes both the racemic mixtures and the pure optical isomers of the compounds of Formula I.

In the synthesis, depending on whether racemic mixtures or optically active compounds corresponding to Formula II are used as the starting materials, the compounds of Formula I are obtained in the form of racemates or as optically active compounds. The optically active compounds can also be obtained from the racemic mixtures in known fashion, for example, by chromatographic separation on chiral separating media or by reaction with suitable optically active acids, for example tartaric acid, and subsequent separation of the recovered salts into their optically active antipodes by fractional crystallization.

The 3-amino-2,3,4,5-tetrahydro-1-benzoxepin-5-ol compounds of Formula II are known from U.S. 4,279,904, and may be produced according to the methods described in this patent, which is hereby incorporated herein by reference.

The compounds of Formula I and their pharmacologically acceptable acid addition salts possess interesting pharmacological properties, particularly those typical of antidepressives. The new compounds are distinguished by marked antidepressive characteristics and have a favorable activity profile and good physiological acceptability. In addition, the new compounds also have characteristics which advantageously affect stomach motility.

The antidepressive activity of the compounds of Formula I is indicated by standard pharmacological tests in animals. For example, the compounds possess antagonistic activity against hypothermia induced in a mouse by tetrabenazine.

DESCRIPTION OF PHARMACOLOGICAL TEST METHODS

1. Determination of Minimum Toxic Dose

Male mice weighing 20 to 25 g were administered per os maximum doses of 300 mg/kg of the test substance. The animals were carefully observed for three hours for toxic symptoms. During a period of 24 hours following the administration all symptoms and deaths were recorded. Side reactions were likewise observed and recorded. When death or strong toxic symptoms were observed, further mice were administered increasingly smaller doses. The lowest dose which produced death or strong toxic symptoms is given as the minimum toxic dose.

2. Determination of the Tetrabenazine Antagonism in Mice

The antagonistic effect of the test substances on the hypothermia induced by tetrabenazine was determined in male mice having a body weight of 18 to 26 g, which had been kept without food for 16 hours at a room temperature of 22 degrees C. To produce hypothermia a dose of 45 mg/kg tetrabenazine suspended in a volume of 10 ml/kg of a 2 percent tylose solution was administered i.p. to the mice. Sixty minutes after the tetrabenazine administration, the test substances were administered per os in a volume of 10 ml/kg of a 2 percent tylose solution to the animals. To a control group, only the tylose solution was administered per os. The initial body temperature of the animals was measured rectally with a thermistor probe immediately before the tetrabenazine administration. The body temperature measurements were repeated 1, 2 and 3 hours after the administration of the test substance. An average value was calculated from the temperature values determined 1, 2 and 3 hours after administration of the test substance or placebo. The difference between this calculated average value and the initial body temperature of the animals indicated the temperature decrease caused by the tetrabenazine. In the animal groups treated with the antidepressively active test substances, the temperature decrease is smaller than in the control animal group treated only with the placebo. The reduction of the temperature decrease produced by the test substances is indicated in percent with reference to the temperature decrease measured in the control group and represents an index of the antidepressive activity of the substances. The following table sets forth the results obtained according to the aforedescribed test methods. The example numbers given for the compounds of Formula I refer to the following synthesis examples.

| Example No. | Minimum Toxic Dose mg/kg mouse | Antagonism against Tetrabenazine Induced Hypothermia | |
|---|---|---|---|
| | | Dose μmol/kg | % Decrease of the Hypothermia |
| 1 | 100 | 31.6 | 54 |
| 5 | 300 | 46.4 | 13 |
| 6 | 200 | 46.4 | 47 |
| 8 | 100 | 46.4 | 36 |
| 10 | 300 | 46.4 | 51 |
| 11 | >300 | 46.4 | 28 |
| 12 | 300 | 46.4 | 14 |
| 14 | 100 | 46.4 | 36 |
| 16 | 200 | 46.4 | 29 |
| 17 | 100 | 46.4 | 46 |

Based on the activities described above, the compounds of Formula I and their pharmacologically acceptable acid addition salts are useful as medicaments in the treatment and prophylaxis of illnesses and functional disturbances of the central nervous system, particularly depressive illnesses.

The dosage to be utilized in any given case will, of course, vary depending on the identity of the substance used, the type of condition to be treated and the form of administration. For example, parenteral formulations will generally contain less active ingredient than oral preparations. In general, however, dosage forms with an active substance content of from 2 to 30 mg per individual dose are suitable for administration to large mammals.

As medicaments, the compounds of Formula I and their physiologically acceptable acid addition salts may be contained with the usual pharmaceutical additives in galenic preparations such as, for example, tablets, capsules, suppositories or solutions. These galenic preparations may be produced according to known methods using conventional solid carriers, such as, for example, lactose, starch or talcum or liquid diluting agents, such as, for example, water, fatty oils or liquid paraffins, and using conventional pharmaceutical auxiliary agents, for example, tablet disintegration agents, solubilizers or preservatives.

The following examples will illustrate the invention in further detail, however, without limiting its scope in any way.

EXAMPLE 1

3-methylamino-2,3-dihydro-1-benzoxepine 23.0 g of 3-methylamino-2,3,4,5-tetrahydro-1-benzoxepin-5-ol hydrochloride were heated to 100 degrees C. for 30 minutes with stirring in 50 ml of 32 percent aqueous hydrochloric acid solution. Subsequently, the solution was poured over 100 g of ice, and the mixture was rendered alkaline with 70 ml of 25 percent aqueous ammonia solution. The mixture was thereafter extracted once with 100 ml and four times with 25 ml portions of methylene chloride. The combined methylene chloride extracts were dried over sodium sulfate, and the solvent was distilled off under reduced pressure. 17.4 g of 3-methylamino-2,3-dihydro-1-benzoxepine were obtained as a colorless oil.

The oily base obtained as described above was dissolved in 25 ml isopropanol, and gaseous hydrogen chloride was introduced into the solution to form the hydrochloride. After cooling, the precipitated 3-methylamino-2,3-dihydro-1-benzoxepine hydrochloride was removed by filtration and recrystallized from isopropanol. Melting point: 168°–170 degrees C.

EXAMPLE 2

7,8-dimethyl-3-methylamino-2,3-dihydro-1-benzoxepine 10.0 g of 7,8-dimethyl-3-methylamino-2,3,4,5-tetrahydro-1benzoxepin-5-ol were dissolved in 50 ml of methanol saturated with hydrogen chloride, and the solution was heated at reflux for two hours with stirring. Subsequently, the solution was evaporated under vacuum; the residue was dissolved in a 25 percent aqueous ammonia solution, and the alkaline ammonia solution was worked up as described in Example 1. 7.9 g of 7,8-dimethyl-3-methylamino-2,3-dihydro-1-benzoxepine hydrochloride were obtained. Melting point: 216–218 degrees C.

EXAMPLE 3

3-butylamino-2,3-dihydro-1-benzoxepine 15.3 g 3-butylamino-2,3,4,5-tetrahydro-1-benzoxepin-5-ol hydrochloride were stirred for four hours at room temperature in 80 ml of an 85 percent aqueous phosphoric acid solution. Subsequently, the solution was poured over 100 g of ice, and the mixture was worked up as described in Example 1. 12.1 g of 3-butylamino-2,3-dihydro-1-benzoxepine hydrochloride were obtained. Melting point: 138 degrees C.

EXAMPLE 4

3-methylamino-2,3-dihydro-1-benzoxepine 1.93 g of 3-methylamino-2,3,4,5-tetrahydro-1-benzoxepin-5-ol were added to 25 ml of ethylene glycol dimethyl ether and reacted with 1.5 g aluminum trichloride while cooling with ice. Subsequently, the reaction mixture was heated for 18 hours at boiling temperature. Thereafter, the solvent was evaporated; the residue was dissolved in water, and the solution was reacted with diluted sodium hydroxide solution and extracted with methylene chloride. The methylene chloride extract was evaporated, and the 3-methylamino-2,3-dihydro-1-benzoxepine which remained as a residue was converted to its hydrochloride as described in Example 1, and this was recrystallized from a methanol/ether mixture. 1.9 g of 3-methylamino-2,3-dihydro-1-benzoxepine hydrochloride were obtained. Melting point: 168°–170 degrees C.

The 3-amino-2,3-dihydro-1-benzoxepine compounds listed in the following table were produced by elimination of water from corresponding 3-amino-2,3,4,5-tetrahydro-1-benzoxepin-5-ols according to the procedures described in the foregoing examples.

| Example No. | $R_1/R_2$ | | $R_3-N-R_4$ | Salt | MP °C. |
|---|---|---|---|---|---|
| 5 | H | H | $H-N-(CH_2)_2-phenyl$ | HCl | 224–227 (D) |
| 6 | H | H | $H-N-CH(CH_3)_2$ | HCl | 203 |
| 7 | H | H | $H-N-C_2H_5$ | HCl | 177–179 |
| 8 | H | H | pyrrolidino | HBr | 136–138 |
| 9 | H | H | $H-N-CH_2-phenyl$ | HCl | 231–233 (D) |
| 10 | H | H | $C_2H_5-N-C_2H_5$ | Cyc | 88–90 |
| 11 | H | H | morpholino | HCl | 178–180 |
| 12 | H | H | 4-benzylpiperazino | 2 HCl | 258–260 |
| 13 | H | H | piperidino | HBr | 160–162 |
| 14 | 7-Cl | H | $H-N-CH_3$ | HCl | 208–209 |

-continued

| Example No. | R₁/R₂ | | $R_3-N-R_4$ | Salt | MP °C. |
|---|---|---|---|---|---|
| 15 | 7-Cl | 8-CH₃ | H—N—CH₃ | HCl | 243-254 |
| 16 | 7-C₂H₅ | H | H—N—CH₃ | HCl | 238-240 (D) |
| 17 | H | H | CH₃—N—C₂H₅ | HBr | 126-128 |
| 18 | H | H | H—N—H | HCl | 220-223 (D) |
| 19 | H | H | CH₃—N—CH₃ | Mal | 135-137 |
| 20 | 8-CF₃ | H | H—N—CH₃ | Ba | Oil |
| 21 | 7-NO₂ | H | H—N—CH₃ | Ba | Oil |
| 22 | 7-Cl | 8-Cl | H—N—CH₃ | HCl | 234-235 (D) |
| 23 | 8-Cl | H | H—N—CH₃ | HCl | 210-211 (D) |
| 24 | 7-Br | H | H—N—CH₃ | HCl | 258-260 (D) |
| 25 | 7-OCH₃ | H | H—N—CH₃ | Ba | Oil |
| 26 | 8-OCH₃ | H | H—N—CH₃ | Ba | Oil |
| 27 | H | H | H—N—(CH₂)₂—OCH₃ | HCl | 88-90 |
| 28 | H | H | H—N—(CH₂)₂—OH | Mal | 98-99 |
| 29 | H | H | 4-methylpiperazino | 2 HCl | 225-227 (D) |
| 30 | H | H | CH₃—N—CH₂—(2-Cl—phenyl) | HCl | 180-181 |
| 31 | H | H | CH₃—N—CH₂—(3-CH₃O—phenyl) | HCl | 176-177 |
| 32 | H | H | H—N—CH₂—(4-CH₃—phenyl) | Mal | 125-127 |
| 33 | H | H | H—N—(CH₂)₃—N(CH₃)₂ | 2 HCl | 199-201 |

| Example No. | $R_1/R_2$ | $R_3\text{—}\underset{\underset{CH_3\text{—}N\text{—}CH_2\text{—}(2,4\text{-di-Cl—phenyl})}{\mid}}{N}\text{—}R_4$ | Salt | MP °C. |
|---|---|---|---|---|
| 34 | H   H | | HCl | 144–146 |

HCl = hydrochloride
Mal = Malinate
Cyc = Cyclohexylaminosulfonate
D = with decomposition
HBr = hydrobromide
Ba = base

EXAMPLE I

Tablets containing 3-methylamino-2,3-dihydro-1-benzoxepine hydrochloride

Tablets were produced having the following composition per tablet:
3-methylamino-2,3-dihydro-1-benzoxepine hydrochloride: 20 mg
corn starch: 60 mg
lactose: 135 mg
gelatine (10 percent solution): 6 mg
The active compound, the corn starch, and the lactose were thickened with the 10 percent gelatine solution. The paste was comminuted, and the resulting granulate was disposed on a suitable sheet and dried. The dried granulate was passed through a crusher and mixed in a mixer with the following additional additives:
talcum: 5 mg
magnesium stearate: 5 mg
corn starch: 9 mg
and then pressed into 240 mg tablets.

The foregoing description and examples have been set forth merely to illustrate the invention and are not intended to limit its scope. Since modifications of the described embodiments incorporating the spirit and substance of the invention may occur to persons skilled in the art, the scope of the invention is to be limited solely with respect to the following claims and equivalents.

We claim:

1. A 3-amino-2,3-dihydro-1-benzoxepine compound corresponding to the formula:

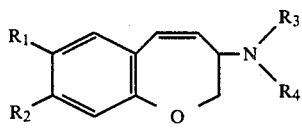

wherein
R$_1$ represents hydrogen, halogen, lower alkyl or lower alkoxy, and
R$_2$ represents hydrogen, halogen, lower alkyl or lower alkoxy, or
one of the substituents R$_1$ and R$_2$ is hydrogen and the other represents a nitro group or trifluoromethyl group,
R$_3$ represents hydrogen, a lower alkyl group or a lower alkyl group which is substituted on a carbon atom not bound to nitrogen by hydroxy, lower alkoxy, or a phenyl group corresponding to Formula a

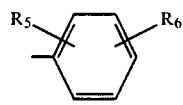

wherein
R$_5$ represents hydrogen, halogen, lower alkyl or lower alkoxy, and
R$_6$ represents hydrogen, halogen, lower alkyl or lower alkoxy,
or by an amino group corresponding to Formula b

wherein
R$_7$ represents hydrogen or lower alkyl, and
R$_8$ represents hydrogen or lower alkyl, and
R$_4$ represents hydrogen or lower alkyl, or
R$_3$ and R$_4$ together with the nitrogen atom to which they are bonded form a saturated 5 member heterocycle or a saturated 6 member heterocycle which may contain as a second heteroatom oxygen, sulfur or an =NR$_{10}$ group in which R$_{10}$ represents hydrogen, lower alkyl, benzyl or benzyl substituted in the phenyl ring with 1 or 2 substituents selected from halogen, lower alkyl, or lower alkoxy, and their acid addition salts.

2. A 3-amino-2,3-dihydro-1-benzoxepine compound according to claim 1, wherein R$_1$ represents hydrogen, halogen, lower alkyl or lower alkoxy, R$_2$ represents hydrogen, halogen, lower alkyl or lower alkoxy, R$_3$ represents hydrogen or a lower alkyl group, and R$_4$ represents hydrogen or a lower alkyl group.

3. A 3-amino-2,3-dihydro-1-benzoxepine compound according to claim 2, wherein R$_1$ represents hydrogen, chlorine, bromine or lower alkyl with 1 or 2 carbon atoms, and R$_2$ represents hydrogen, chlorine, bromine or lower alkyl with 1 or 2 carbon atoms.

4. 3-methylamino-2,3-dihydro-1-benzoxepine and its acid addition salts.

5. A pharmaceutical composition comprising an effective antidepressive amount of a compound according to claim 1 and a conventional pharmaceutical carrier.

* * * * *